(12) United States Patent
Hayashi

(10) Patent No.: US 6,415,232 B1
(45) Date of Patent: Jul. 2, 2002

(54) CHROMATOGRAM ANALYZER

(75) Inventor: Hidechika Hayashi, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 09/393,267

(22) Filed: Sep. 10, 1999

(30) Foreign Application Priority Data

Sep. 10, 1998 (JP) .......................................... 10-256362
Sep. 10, 1998 (JP) .......................................... 10-256363

(51) Int. Cl.$^7$ .............................................. G01N 31/00
(52) U.S. Cl. ...................... 702/22; 73/23.35; 73/23.42; 436/52; 436/161; 702/23; 702/32; 702/85
(58) Field of Search .......................... 702/22, 23, 32, 702/85; 73/23.35, 23.42; 436/52, 161

(56) References Cited

U.S. PATENT DOCUMENTS

| | | | | |
|---|---|---|---|---|
| 3,555,260 A | * | 1/1971 | Karohl | 702/32 |
| 3,607,075 A | * | 9/1971 | Wolf | 436/52 |
| 3,633,404 A | * | 1/1972 | Chandler | 73/23.42 |
| 4,468,742 A | * | 8/1984 | Jenden et al. | 702/23 |
| 5,001,071 A | * | 3/1991 | Morabito et al. | 436/161 |
| 5,436,166 A | * | 7/1995 | Ito et al. | 436/161 |
| 5,644,503 A | * | 7/1997 | Ito et al. | 702/22 |
| 5,804,142 A | * | 9/1998 | Ito et al. | 702/23 |
| 5,905,192 A | * | 5/1999 | Wikfors et al. | 73/23.35 |
| 6,112,161 A | * | 8/2000 | Dryden et al. | 702/85 |
| 6,134,503 A | * | 10/2000 | Matsumoto et al. | 702/23 |

OTHER PUBLICATIONS

U.S. application No. 09/393,194, filed Sep. 10, 1999.
U.S. application No. 09/393,267, filed Sep. 10, 1999.

* cited by examiner

*Primary Examiner*—John S. Hilten
*Assistant Examiner*—John Le
(74) *Attorney, Agent, or Firm*—Oblon, Spivak, McClelland, Maier & Neustadt, P.C.

(57) ABSTRACT

A chromatogram analyzer is provided which analyzes a chromatogram obtained by applying a sample containing an analyte. The chromatogram analyzer can be used after peak detection, for example, based on predicted peak emergence times for respective analytes of interest and can determine proper baselines even in the presence of peaks attributable to components other than the analytes or ghost peaks. The chromatogram analyzer is used for an analysis of a chromatogram developed by chromatography, namely by separating and detecting analytes in a sample. Although chromatography is divided into various types of liquid chromatography and gas chromatography according to the principles for separation and development, a chromatogram obtained by any type of chromatography can be analyzed. For example, an electrophoretically obtained result stained with a proper dye can be analyzed by using the present invention after photometric scanning.

11 Claims, 15 Drawing Sheets

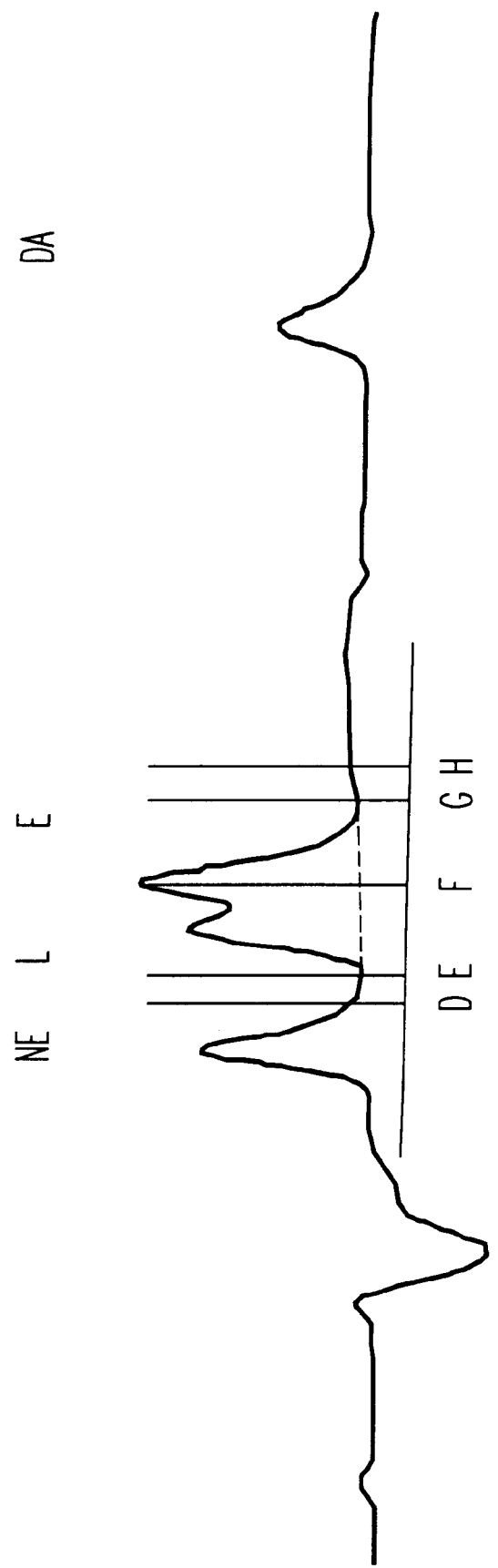

CHROMATOGRAM ANALYZER

BACKGROUND OF THE INVENTION

1. Field of the Invention

The present invention relates to an analyzer which analyzes a chromatogram obtained by applying a sample containing an analyte to liquid chromatography or gas chromatography using a column or the like.

2. Discussion of Background

In qualitative and quantitative analyses of analytes, for example, by liquid chromatography, chromatograms obtained are analyzed by detecting analyte peaks and determining their heights, widths and areas.

Chromatograms are analyzed by detecting peaks emerging during elution of analytes and then matching of the detected peaks with expected components (hereinafter referred to as the first method), or by seeking peaks around predicted peak emergence times (reference peak emergence times) for respective analytes of interest (hereinafter referred to as the second method).

In the first method, peaks attributable to unexpected unknown components as well as peaks attributable to expected components are detected, and peaks are defined as the highest points between the initial points and terminal points of the peaks defined on the basis of the slope of the chromatogram. However, noises which are not attributable to any components in the sample are likely to be detected as peaks. Also, there is a problem that the initial points and terminal points of peaks can not be detected correctly with drifting baselines (unstable baselines) because the slope of the chromatogram can not be sensed correctly.

In contrast, the second method has an advantage that peaks attributable to expected analytes can be detected correctly, though other peaks are not detected by the second method.

Still, for correct analyses of chromatograms, proper baseline establishment is needed in addition to correct detection of analyte peaks.

In conventional peak analyses, a baseline is defined as the straight line joining first and second baseline points provided on the chromatogram before and after the emergence time of a detected analyte peak with a certain time gap, for example, corresponding to a multiple of the peak width at half the peak height (the half width).

Therefore, if a baseline point determination of the baseline of an analyte falls inside a peak attributable to another component or a ghost peak (resulting from, for example, a switching valve operation for sample injection in liquid chromatography), the level of the chromatogram at the baseline point shifts from the level of the true baseline, and consequently, for example, in a peak analysis based on peak height, the peak height obtained as the result of the analysis is different from the true value. Because peaks attributable to components other than analytes and ghost peaks emerge at different times in different sizes depending on not only the kinds of the components and analysis conditions but also analysis environments such as room temperature, there is a problem that it is necessary to determine new baseline points which do not fall inside these peaks every time the analysis environments change in order to give a proper baseline.

SUMMARY OF THE INVENTION

Accordingly, the object of the present invention is to provide a chromatogram analyzer for use after peak detection, for example, based on predicted peak emergence times (reference peak emergence times) for respective analytes of interest, which can determines proper baselines even in the presence of peaks attributable to components other than the analytes or ghost peaks.

In order to achieve the above-mentioned object, according to claim 1 of the present application (hereinafter referred to as the first aspect of the present invention), the present invention provides a chromatogram analyzer which analyzes a chromatogram obtained by applying a sample containing an analyte, which comprises a first storage means which stores a baseline detection starting time (tb1) and a baseline detection ending time (tb2) (wherein tb1<tb2) for determination of a baseline used for analysis of an analyte peak; a second storage means which stores a chromatogram of the analyte; a first arithmetic means which detects an analyte peak and its emergence time (tx, wherein tb1<tx<tb2) on the chromatogram; and a second arithmetic means which detects a first baseline point between tb1 and tx by using a function having at least one of the level, the slope, the curvature and the gap from tx of the chromatogram at a particular point as the variables, detects a second baseline point between tx and tb2 by using a function having at least one of the level, the slope, the curvature and the gap from tx of the chromatogram at a particular point as the variables and gives a straight line passing through the first baseline point and the second baseline point as the baseline.

According to claim 2 of the present application (hereinafter referred to as the second aspect of the present invention), the present invention also provides a chromatogram analyzer which analyzes a chromatogram obtained by applying a sample containing an analyte, which comprises a first storage means which stores a baseline detection starting time (tb1) and a baseline detection ending time (tb2) (wherein tb1<tb2) for determination of a baseline used for analysis of an analyte peak; a second storage means which stores a chromatogram of the analyte; a first arithmetic means which detects an analyte peak and its emergence time (tx, wherein tb1<tx<tb2) on the chromatogram; and a second arithmetic means which detects a first baseline point between tb1 and tx by using a function having at least one of the level, the slope, the curvature and the gap from tx of the chromatogram at a particular point as the variables, defines the point on the chromatogram at tb2 as a second baseline point and gives a straight line passing through the first baseline point and the second baseline point as the baseline.

According to claim 3 of the present application (hereinafter referred to as the third aspect of the present invention), the present invention further provides a chromatogram analyzer which analyzes a chromatogram obtained by applying a sample containing an analyte, which comprises a first storage means which stores a baseline detection starting time (tb1) and a baseline detection ending time (tb2) (wherein tb1<tb2) for determination of a baselines used for analysis of an analyte peak; a second storage means which stores a chromatogram of the analyte; a first arithmetic means which detects an analyte peak and its emergence time (tx, wherein tb1<tx<tb2) on the chromatogram; and a second arithmetic means which defines the point on the chromatogram at tb1 as a first baseline point, detects a second baseline point between tx and tb2 by using a function having at least one of the level, the slope, the curvature and the gap from tx of the chromatogram at a particular as the variables and gives a straight line passing through the first baseline point and the second baseline point as the baseline.

According to claim 4 of the present application (hereinafter referred to as the fourth aspect of the present invention), the present invention further provides a chromatogram analyzer which analyzes a chromatogram obtained by applying a sample containing an analyte, which comprises a first storage means which stores a baseline detection starting time (tb1) for determination of a baseline used for analysis of an analyte peak; a second storage means which stores a chromatogram of the analyte; a first arithmetic means which detects an analyte peak and its emergence time (tx, wherein tb1<tx) on the chromatogram; and a second arithmetic means which detects a baseline point between tb1 and tx by using a function having at least one of the level, the slope, the curvature and the gap from tx of the chromatogram at a particular point as the variables and gives a straight line parallel to the time axis and passing through the baseline point as the baseline.

According to claim 5 of the present application (hereinafter referred to as the fifth aspect of the present invention), the present invention further provides a chromatogram analyzer which analyzes a chromatogram obtained by applying a sample containing an analyte, which comprises a first storage means which stores a baseline detection ending time (tb2) for determination of a baseline used for analysis of an analyte peak; a second storage means which stores a chromatogram of the analyte; a first arithmetic means which detects an analyte peak and its emergence time (tx, wherein tx<tb2) on the chromatogram; and a second arithmetic means which detects a baseline point between tx and tb2 by using a function having at least one of the level, the slope, the curvature and the gap from tx of the chromatogram at a particular point as the variables and gives a straight line parallel to the time axis and passing through the baseline point as the baseline.

BRIEF DESCRIPTION OF THE DRAWINGS

FIG. 15 shows the baseline determined by the analyzer of the present invention in an analysis of the peak attributable to a catecholamine, epinephrine.

DETAILED DESCRIPTION OF THE PREFERRED EMBODIMENTS

Figure 1:
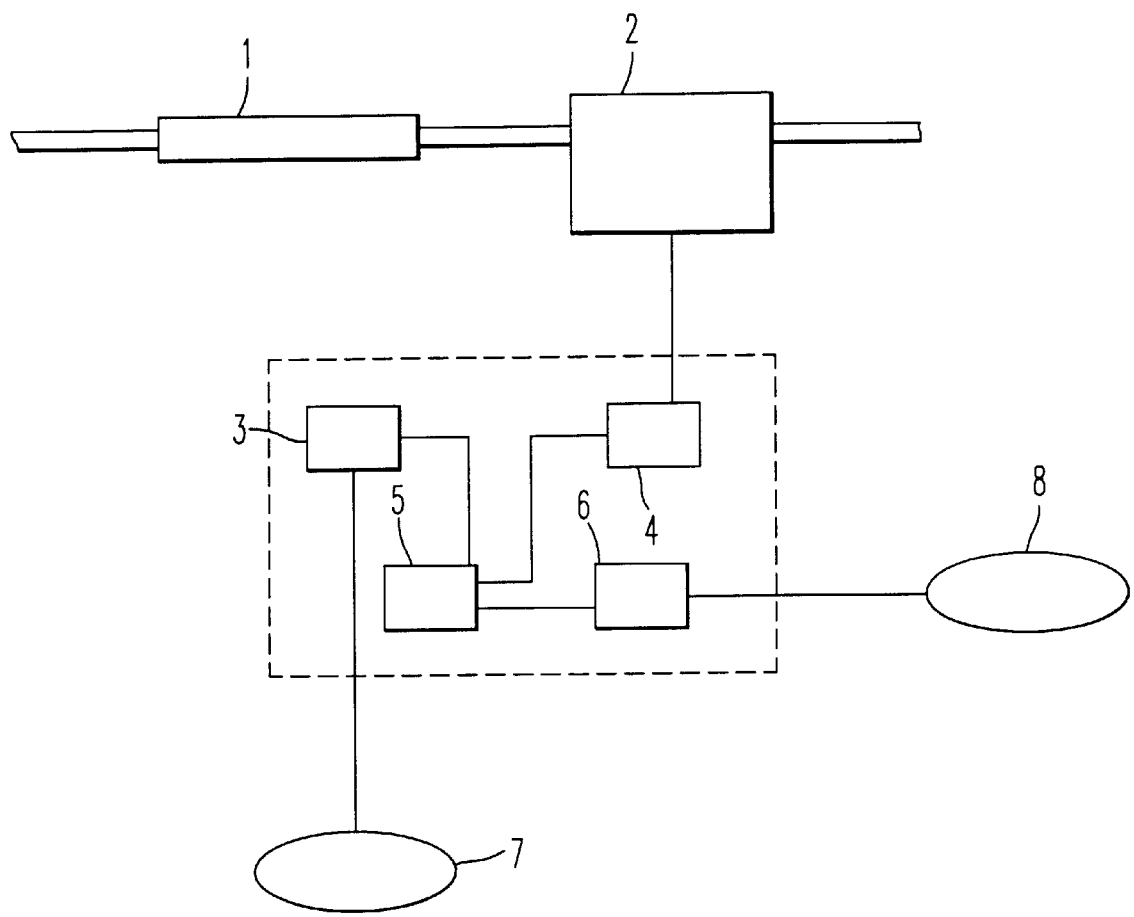
FIG. 1 shows an outline of the analyzer of the present invention.

Now, the present invention will be described in detail.

The chromatogram analyzer of the present invention is used for an analysis of a chromatogram developed by chromatography, namely by separating and detecting analytes in a sample. Although chromatography is divided into various types of liquid chromatography and gas chromatography according to the principles for separation and development, a chromatogram obtained by any type of chromatography can be analyzed. For example, an electrophoretically obtained result stained with a proper dye can be analyzed by using the present invention after photometric scanning.

It is preferred to perform smoothing by simple running averaging, polynomial fitting, the Fourier transform or a wavelet transform or spike noise removal by simple spike removal, the Fourier transform or a wavelet transform on a chromatogram before the chromatogram is analyzed by the analyzer of the present invention. Noise removal by these processings makes the levels of the tops and bottoms of analyte peaks in chromatograms less susceptible to noise, and affords more reliable analysis results.

The simple running average is expressed by $Y_n=\mathrm{Sum}(X_i)/m$ (wherein Sum is a function which adds up consecutive data $X_i$, and m is the number of the data added). Polynomial fitting is expressed by $Y_n=\mathrm{Sum}(K_i \times X_i)/\mathrm{Sum}(K_i)$ (wherein Sum and $X_i$ are the same as defined above, and $K_i$ is a coefficient which is so determined as to fit the data to a quadratic or cubic expression, for example, by the Savitzky-Golay method). The Fourier transform comprises multiplying the Fourier transformed data in the frequency domain by a window function which. cuts off high frequency components and taking the inverse Fourier transform of the product. The wavelet transform is disclosed in Analytical Chemistry, vol.69, No.1, pp.78–90, 1997. Simple spike removal may be conducted by the median method (in which the median of a series of three to five data, $Y=\mathrm{Median}(X_i)$, is taken)

In the present invention, the second arithmetic means detect the same first and second baseline points whether they are calculated after smoothing by simple running averaging or by using the average level of points of chromatogram around a particular point as the level of the chromatogram at the point.

The analyzer of the present invention is used for baseline determination after identification of analyte peaks in a chromatogram at the initial stage of the analysis of the chromatogram. However, a means for detection of analyte peaks may be added to the analyzer of the present invention without any restriction.

The arithmetic means for detection of analyte peaks may be a conventional means for peak detection, but may have the structure exemplified below. Firstly, peak detection starting times (tp1) and peak detection ending times (tp2) for peak detection are stored in an appropriate storage means which may be a rewritable storage medium such as an ordinary memory or a flash memory, for example, through an input means such as a keyboard. For this purpose, another storage means may be installed in the first arithmetic means, or the first or second storage means in the present invention may be used. The first arithmetic means may be constituted, for example, by a computer or may be unified with the second arithmetic means, which will be mentioned later. tp1 and tp2 are used for detection of analyte peaks to be analyzed in a chromatogram and set for each analyte. They have a relation expressed by tp1<tp2 and may be so determined as to satisfy tp1 <ts<tp2 wherein ts is the reference emergence time of an analyte determined from a chromatogram obtained by applying a sample containing analytes only. More specifically speaking, tp1 and tp2 are determined appropriately by taking into consideration the mode of chromatographic separation used and ts under the analysis environments such as the flow rate of the mobile phase and room temperature and a shift of ts due to change in the analysis environments, namely so as to satisfy tp1<tx<tp2. tp1 and tp2 may be modulated in accordance with the difference between ts and tx after they are determined on the basis of ts so as to satisfy the above-mentioned relation. tp1 and tp2 are preferably determined so that tp2−tp1 is small when components other than analytes are predicted to exist, and so that tp2−tp1 is large when components other than analytes are not predicted to exist. For example, they are determined so that tp2−tp1 corresponds to about from 1 to 2 times the peak width at half the height (half width) of a peak in a chromatogram of a standard sample containing analytes, but they do not need to always satisfy ts−tp1=tp2−ts. Thereafter, the highest point between tp1 and tp2 is defined as the top of an analyte peak.

The first storage means according to the first to fifth aspects of the present invention stores a baseline detection starting time (tb1) and a baseline detection ending time (tb2) for determination of a baseline used for analysis of an analyte peak detected as described above and may be a rewritable storage medium such as an ordinary memory or a flash memory.

According to the first to third aspects of the present invention, the first storage means stores a baseline detection starting time (tb1) and a baseline detection ending time (tb2) for detection of baseline points used for determination of a baseline. tb1 and tb2 satisfy tb1<tb2 and are so determined as to satisfy the relation with tx expressed by tb1<tx<tb2, too. tb1 and tb2 are determined preferably so that a baselines (flat part of a chromatogram other than tops or feet of peaks) appears between tb1 and tx and between tx and tb2 even if there are contaminant peaks, and no negative ghost peaks appear within these ranges. In this case, it is necessary to consider that even if no contaminant peaks or no ghost peaks appear. under particular conditions, some samples may contain different contaminants, or ghost peaks may appear from samples which have changed with time. In general, tb2−tb1 is set at from twice to 6 times, or from 5 to 8 times the peak width at half the peak height (the half width), for example, depending on the predicted positions of contaminant peaks and ghost peaks, but do not have to always satisfy tx−tb1=tb2−tx. Although the analyzer of the present invention can not give peak heights or widths until the baselines are determined, preliminary peak widths obtained from a chromatogram of a standard sample containing analytes only on the basis of roughly determined baselines are input into the first storage means and then output to the second arithmetic means. After the second arithmetic means in the present invention sets baselines, the peak widths obtained on the basis of the baselines may be fed back to the first storage means. Though different tb1 and tb2 are given for each analyte peak, the range from tb1 to tb2, namely tb2−tb1, for each peak may be the same or different. Further, ts−tb1 and tb2−ts may be the same or different.

On the other hand, when there is difference between ts and the actual emergence time for an analyte, corrections based on the difference may be made to tb1 and tb2. Because the amounts of analytes in a sample are unknown, while a standard sample contains known amounts of analytes, the half peak widths are determined preferably by using a standard sample containing predicted amounts of analytes.

To the present inventors' knowledge, when baseline determination is not expected to suffer interference by contaminant peaks or ghost peaks, tb1 and tb2 may be set so as to correspond to positions which are at a distance of the width of an analyte peak at half the peak height, or twice or 3 times as far, from tx. When baseline determination is expected to suffer interference by contaminant peaks or ghost peaks, tb1 and tb2 are preferably set so as to correspond to positions at a distance of three times the width of an analyte peak at half the peak height.

The second storage means stores a chromatogram to be analyzed and may be a rewritable storage medium such as an ordinary memory or a flash memory which preferably stores a detection signal from the detector, for example, in liquid chromatography in real time. The second storage means may be unified with the above-mentioned first storage means. The real time signal storage may be done continuously or intermittently, for example, every second. When a chromatogram is stored intermittently, the time interval for storage is preferably as short as possible. The zero time to be stored may be the time at which a sample is applied to a separation means such as a separation column or the time at which storage of the detection signal is started a certain time after the sample application. When a result of electrophoresis is scanned, migration distance is used instead of time.

The second arithmetic means determines a first baseline point between tb1 and tx and a second baseline point between tx and tb2 by using functions having at least one of the level, the slope, the curvature and the gap from tx of the chromatogram at a particular point as the variables, and gives a straight line passing through the first baseline point and the second baseline point as the baseline. The second arithmetic means may be, for example, a computer.

The functions may, for example, be a function of the level of a chromatogram at a particular point. More specifically, functions which have, preferably, at least two of the level, the slope, the curvature and the gap from tx of the chromatogram at a particular point as the variables and gives the sum of them or the sum of their absolute values, or which are expressed by the combination of their multiplication and addition, may be mentioned. Functions which have at least one of the level, the slope, the curvature and the gap from tx of the chromatogram at a particular point as the variables are preferable to set baseline points which do not fall inside ghost peaks, and functions which have them all as the variables are particularly preferable.

Particularly preferable examples of a function having at least two of or all of the level, the slope, the curvature and the gap from tx of the chromatogram at a particular point as the variables are as follows.

A function represented by (the level of the chromatogram at a particular point)+a×(the absolute slope of the chromatogram)+b×(the absolute curvature of the chromatogram)+c×(((t−tx)/(tb1−tx))$^4$), and a function represented by (the level of the chromatogram at a particular point)×(1+a×(the absolute slope of the chromatogram))×(1+b×(the absolute curvature of the chromatogram))×(1+c×((t−tx)/(tb1−tx)$^4$)

In the above expressions, the slope of the chromatogram is given as the first derivative of the level of the chromatogram at a particular point, and the curvature of the chromatogram is given as the second derivative of the level of the chromatogram. a to c are parameters and positive values or zero. In the case of two or three variables, two or one of the parameters are zero. The term including the parameter c may be c×(((t−tx)/(tb2−tx))$^4$) when tx−tb1 is different from tb2−tx, and may be c×(((t−tx)/(tb2−tx))$^4$) when t>tx. The term including the parameter c may be c×(((t−tx)/(tb2−tx)$^4$) when tx−tb1 is different from tb2−tx. It may be c×(((t−tx)/(tb1−tx))$^4$) when t<tx, and may be c(((t−tx)/(tb2−tx))$^4$) when t>tx.

The parameters in the above expressions can be determined appropriately in accordance with the emergence times, heights and widths of the analyte peak and expected ghost peaks. They may be determined by considering that the positions of analyte peaks in relation to contaminant peaks change in accordance with the emergence times, heights and widths of expected contaminant peaks, the chromatographic temperature and the eluent composition. They may also be determined in accordance with how to determine tb1 and tb2 and the height of the analyte peak.

The parameters in the above mentioned functions may be different depending on whether the chromatogram to be analyzed by the analyzer of the present invention is a chromatogram of an unknown sample which is likely to contain contaminants or a chromatogram of a standard containing no contaminants. Namely, different parameters may be used for an analysis of a chromatogram of a standard sample and an analysis of a chromatogram of an unknown sample, though the same parameters may be used. Especially, in the case of a standard sample, the parameters can be determined by considering the possibility of ghost peaks only because a standard sample contains known amounts of analytes only and does not contains contaminants, and almost the same baseline points are obtained with wide ranges of parameters. In contrast, the parameters in the function for an unknown sample containing unknown amounts of analytes have to be set at appropriate values for proper baseline detection because peak heights can vary drastically or peaks attributable to contaminants may appear.

Of those mentioned above, if the level of the chromatogram is used as a variable, points on the chromatogram which are near the lowest points of the chromatogram between tb1 and tx and between tx and tb2 are detected as baseline points. If the slope of the chromatogram is used as a variable, points on the chromatogram which are not on the slopes of peaks and at which the chromatogram is almost flat are detected as baseline points. If the curvature of the chromatogram is used as a variable, detection of the dip of a negative ghost peak as a baseline point can be avoided. If the gap from tx of the chromatogram at a particular point is used as a variable, points as close as possible to peaks are detected as baseline points. Therefore, although use of the level of the chromatogram at a particular point as the only variable allows detection of baseline points for baseline determination, use of at least two, preferably at least three, more preferably all of them as the variables leads to detection of baseline points for determination of baselines which enables the most accurate analyte quantification even when a baseline in the chromatogram is sloping or when there is a ghost peak.

Namely, the combined use of these variables leads to detection of the lowest points as baseline points basically, but if they are on slopes or at the dips of negative ghost peaks, they are inferior to the points which are not of the lowest levels but at which the chromatogram is flatter. Further, even if tx−tb1 and tb2−tx are fixed at large values due to an expected overlap of the foot of an analyte peak with the foot of another analyte peak or a contaminant peak, when there is actually no overlap between them, it is possible to provide baseline points near the emergence time of the analyte peak and therefore to remove the influences of drifts of baselines.

Thus, the points on a chromatogram between tb1 and tx and between tx and tb2 which minimize the function are defined as the first baseline point and the second baseline point, respectively. Then, the straight line joining the two points is given as the baseline. The baseline determination is followed by calculation of the peak height, peak area or half width of the analyte peak, etc., which may be preformed by the second arithmetic means in the present invention.

According to the second or third aspect of the present invention, the first or second baseline point is detected between tb1 and tx or between tx and tb2 as described above, while the point of the chromatogram at tb2 or tb1 is used as the other baseline point.

According to the fourth or fifth aspect of the present invention, the second arithmetic means uses only the baseline detection starting time (tb1) or the baseline detection ending time (tb2) in the first aspect of the present invention as the only one baseline point, and gives the straight line parallel to the time axis and passing through the baseline point as the baseline.

In the fourth and fifth aspects of the present invention, tb1 or tb2 is determined in the same manner. The first to third aspects of the present invention are effective especially when an analyte peak is close to another analyte peak or a contaminant peak, and the fourth aspect of the present invention is effective especially when a series of analyte peaks or contaminant peaks appear after an analyte peak or when the baseline is drifting after the peak. The fifth aspect of the present invention is effective especially when a series of analyte peaks or contaminant peaks appear before an analyte peak or when the baseline is drifting before the peak. Therefore, the analyzer of the present invention is used according to one of the first to fifth aspects after appropriate selection based on whether there is any peak around an analyte peak in the chromatogram to be analyzed. To this end, the analyzer of the present invention may be constituted by a computer and a storage means so as to cover all the functions according to the first to fifth aspects of the present invention and may analyze a chromatogram by appropriately selecting any one of the aspects.

The analyzer of the present invention may comprise an output means which displays or prints out results of analyses or a means which gives an alert when no peak is detected for an analyte, in addition to various means described above.

Now, the present invention will be described in further detail by referring to Examples. However, it should be understood that the present invention is by no means restricted to these specific Examples.

FIG. 1 illustrates an example of application of the present invention to a chromatogram analyzer for liquid chromatography. In the figure, 1 is a separation column, 2 is a detector, and other chromatographic devices such as a feed pump and a sample injector are omitted.

The analyzer of the present invention, enclosed with a dashed line in the figure, is constituted by one computer including various means. In the figure, 3 is a first storage means, 4 is a second storage means, 5 is a first arithmetic means, and 6 is a second arithmetic means. The first storage means 3 stores input from the keyboard 7, the second storage means 4 stores output (a chromatogram) from the detector 2, the first arithmetic means 5 is connected to the first and second storage means, and the second arithmetic means is connected to the first arithmetic means. The second arithmetic means 6 outputs the result of chromatogram analysis into the printer 8.

Figure 2:
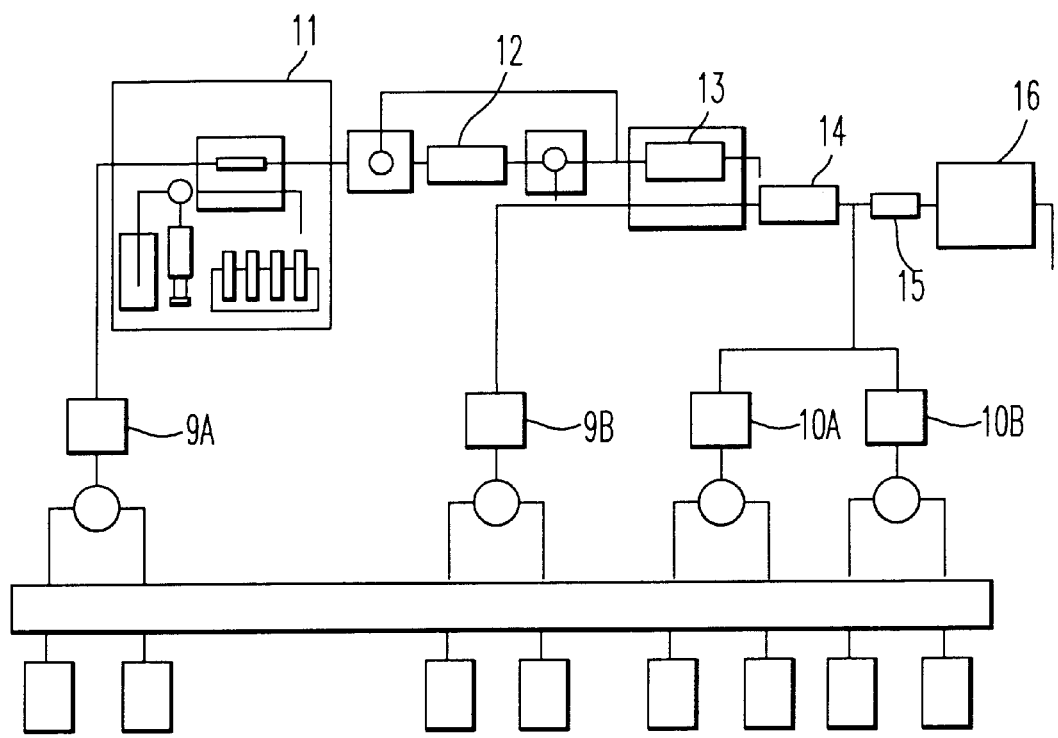
FIG. 2 outlines the liquid chromatograph used in Examples.

FIG. 2 outlines the structure of the liquid chromatograph used in the following Examples. The chromatograph comprises eluent pumps 9a and 9b, reagent pumps 10a and 10b, an automatic sample injector 11, two pre-columns 12 and 13, a separation column 14, a reactor 15 and a fluorometric detector 16, and further an eluent switch valve and a flow switch valve, The analyzer of the present invention is connected to the detector 16.

EXAMPLE 1

FIG. 8 to FIG. 11 graphically show analyses of liquid chromatograms for assay of a catecholainine, epimephrine (E), In the assay, a sample containing catecholamines, norepinephrine (NE), epinephrine (E) and dopamine (DA) at 1 pg/ml each was used after mixed with an equivalent amount of levonordefrin (L) as a contaminant. The liquid chromatograph used was equipped with two pre-columns (the first pre-column 12 was a reversed-phase (ether gel) column of $\phi$ 4.6 mm×75 mm, and the second pre-column 13 was an ion exchange column of $\phi$ 3.0 mm×60 mm) and a separation column 14 which was a reversed-phase (ODS) column ($\phi$ 4.0 mm×150 mm). In the chromatograph, a sample was carried to the first pre-column by an eluent (phosphate buffer (pH 7)) fed by means of the pump 9a (1.0 ml/min), and then another eluent (a mixture of aqueous ammonium nitride and acetonitrile) was fed to the first pre-column by the pump 9a by switching a solenoid valve to elute the retained sample components onto the second pre-column. Then, the sample components retained on the second pre-column was eluted with an eluent (Tris buffer (pH 7) containing ammonium nitrate) fed by the pump 9b (0.7 ml/min) onto the separation column and separated. The components eluted from the separation column were introduced to the reactor 15 after mixed with a fluorescent reagent and converted into a fluorescent derivative by the reaction with DPE (diphenylethylenediamine) as the fluorescent reagent at 90° C. for 3 minutes in the reactor. The fluorescent reagent was fed by means of the pump 10a and the pump 10b (0.25 ml/min each). The fluorescent derivatives of the analytes were monitored by a fluorometric detector at an excitation wavelength of 340 to 360 nm and an emission wavelength of 460 nm to give a chromatogram.

Figure 8:
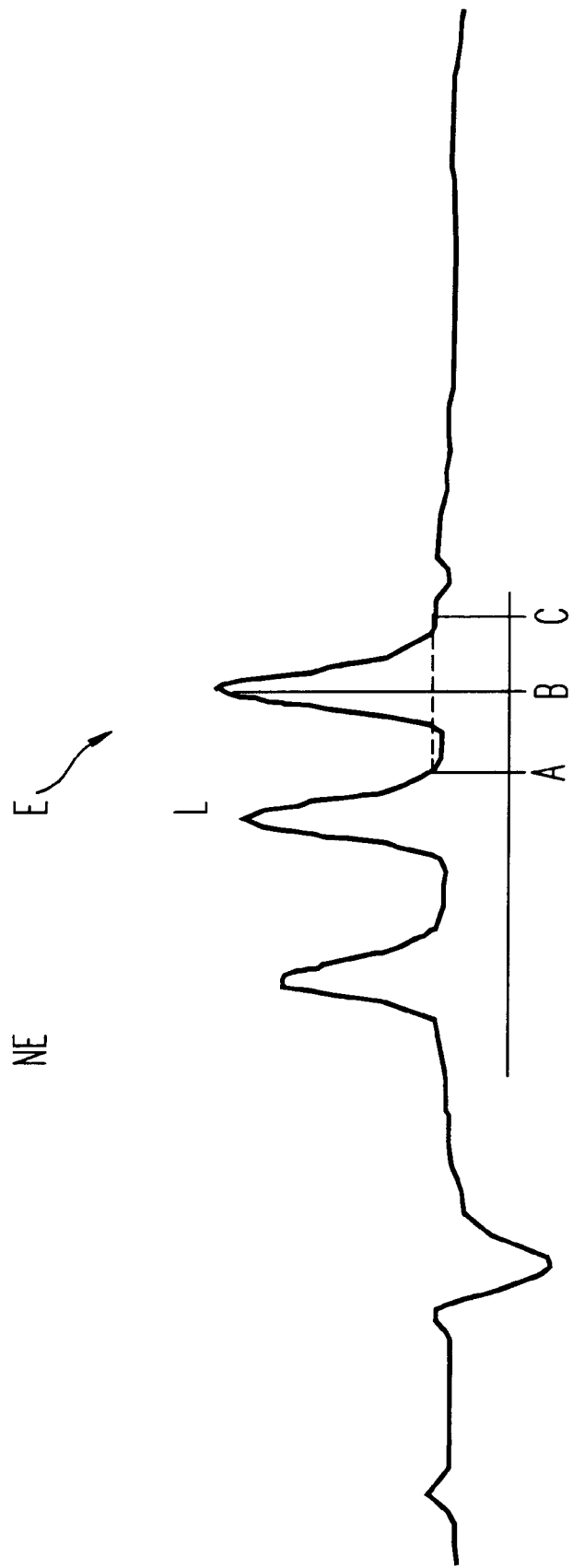
FIG. 8 shows the baseline determined by a conventional analyzer in an analysis of the peak attributable to a catecholamine, epinephrine.
Figure 9:
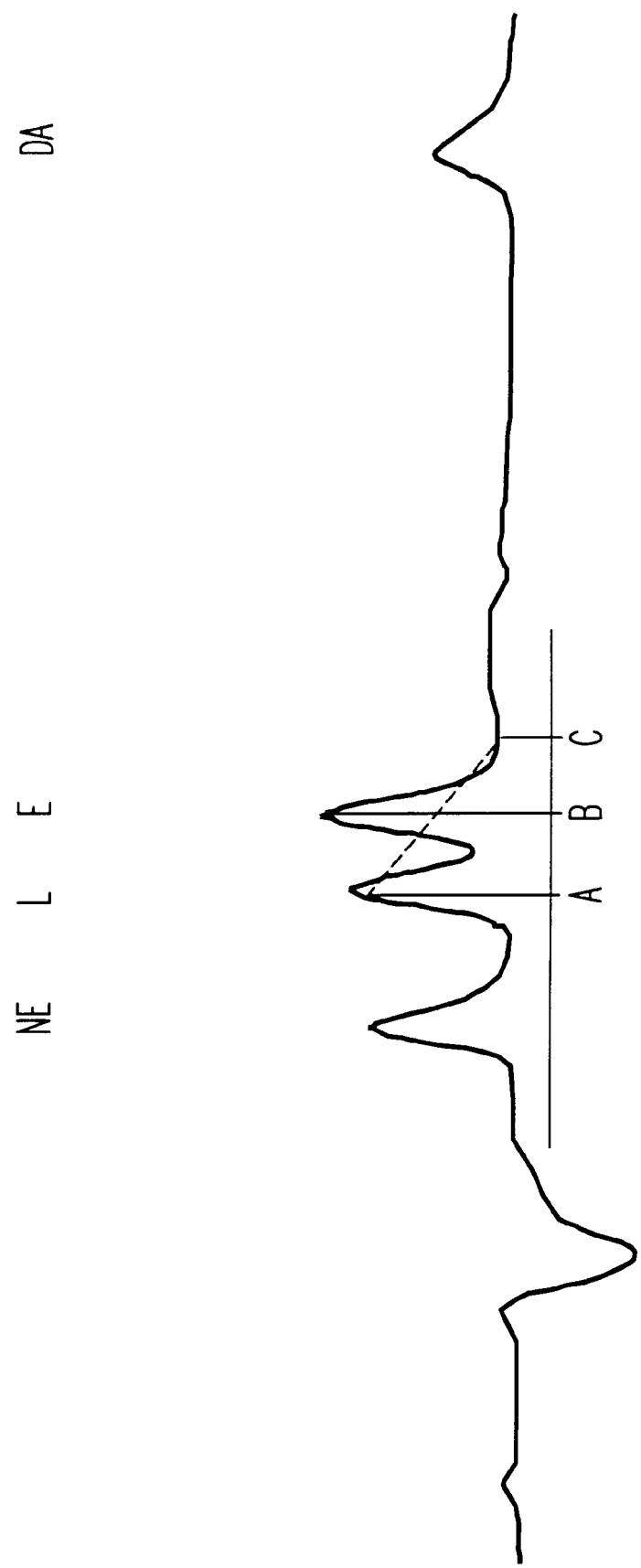
FIG. 9 shows the baseline determined by a conventional analyzer in an analysis of the peak attributable to a catecholamine, epinephrine.
Figure 10:
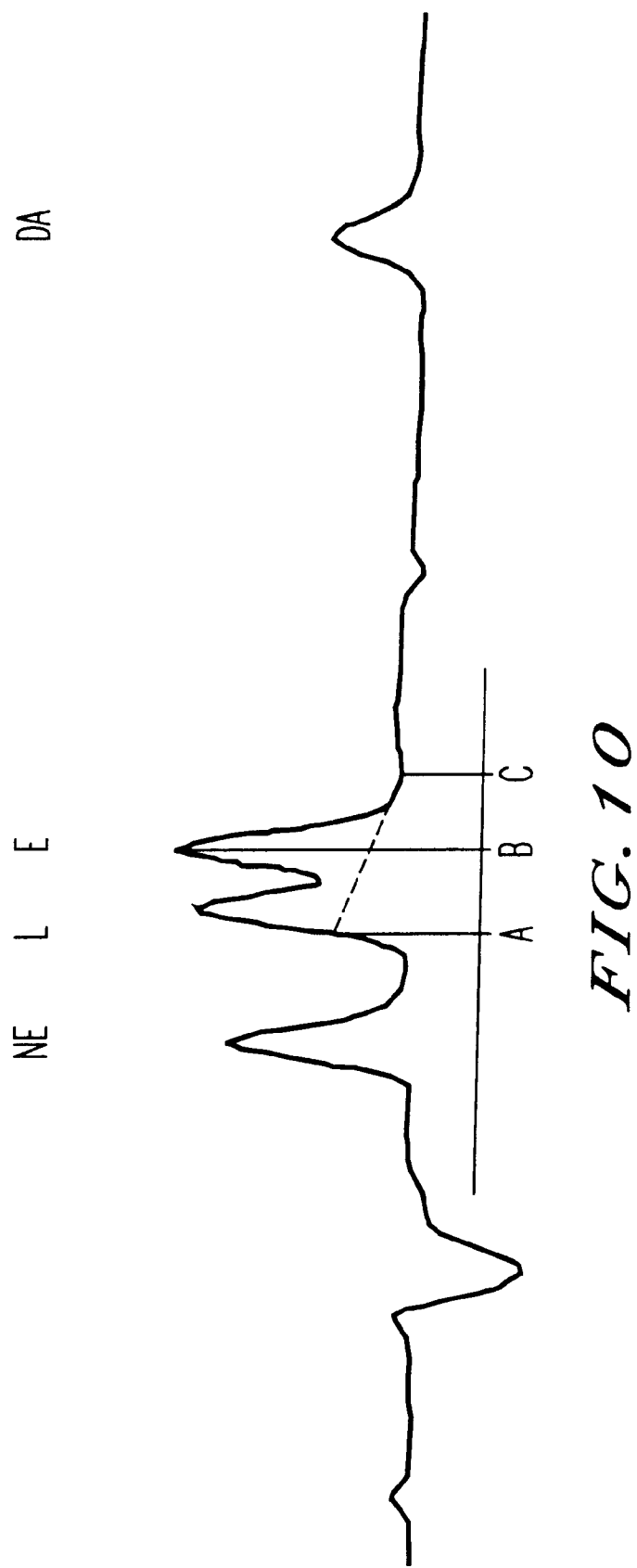
FIG. 10 shows the baseline determined by a conventional analyzer in an analysis of the peak attributable to a catecholamine, epinephrine.
Figure 11:
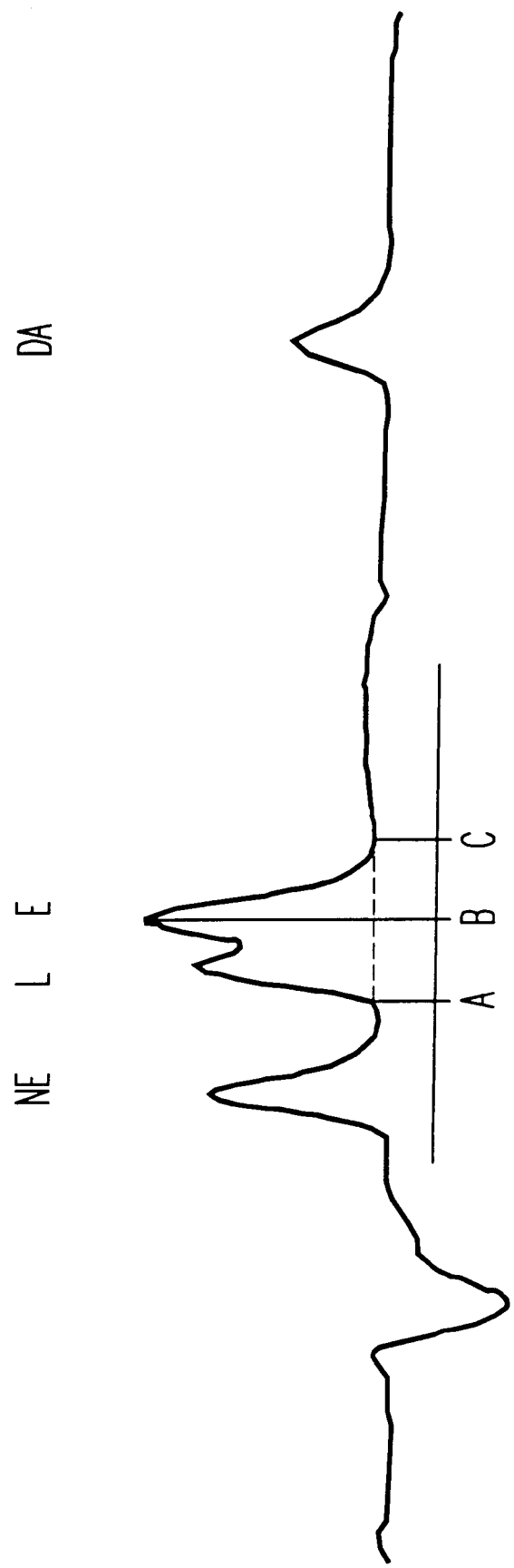
FIG. 11 shows the baseline determined by a conventional analyzer in an analysis of the peak attributable to a catecholamine, epinephrine.
Figure 12:
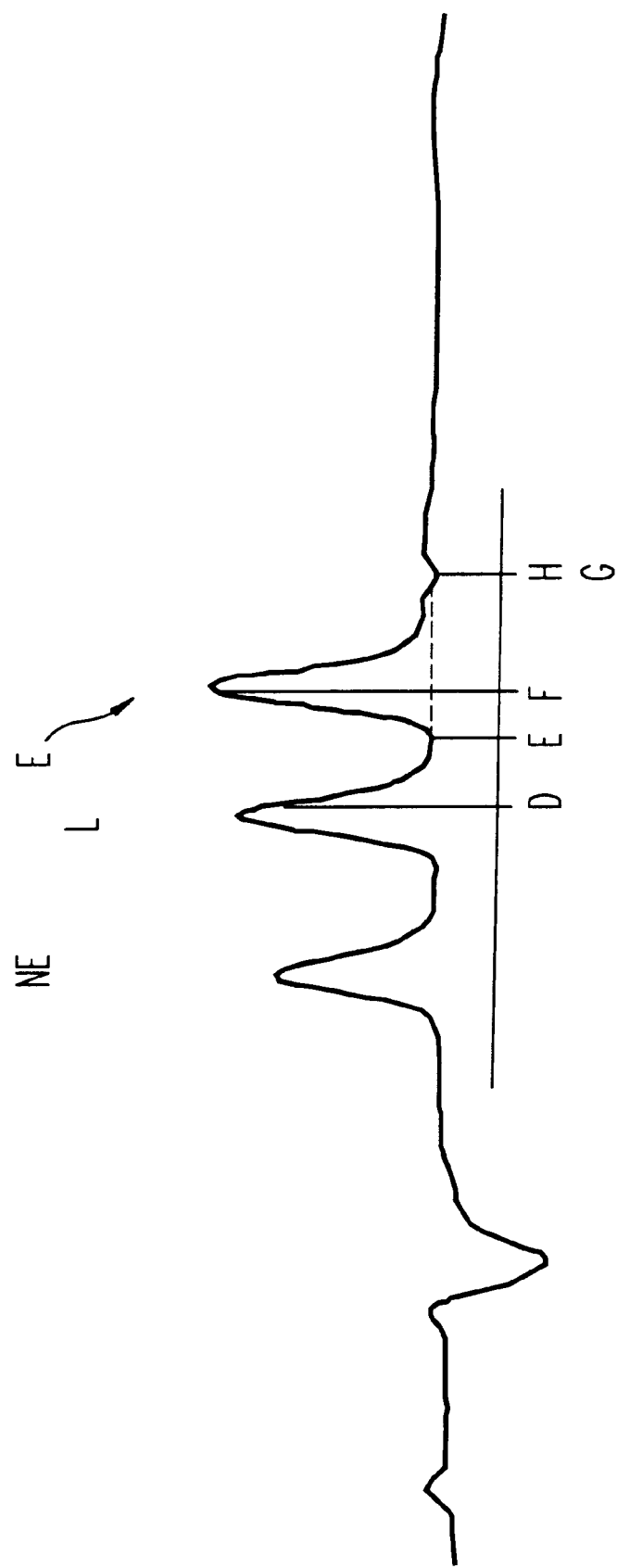
FIG. 12 shows the baseline determined by the analyzer of the present invention in an analysis of the peak attributable to a catecholamine, epinephrine.
Figure 13:
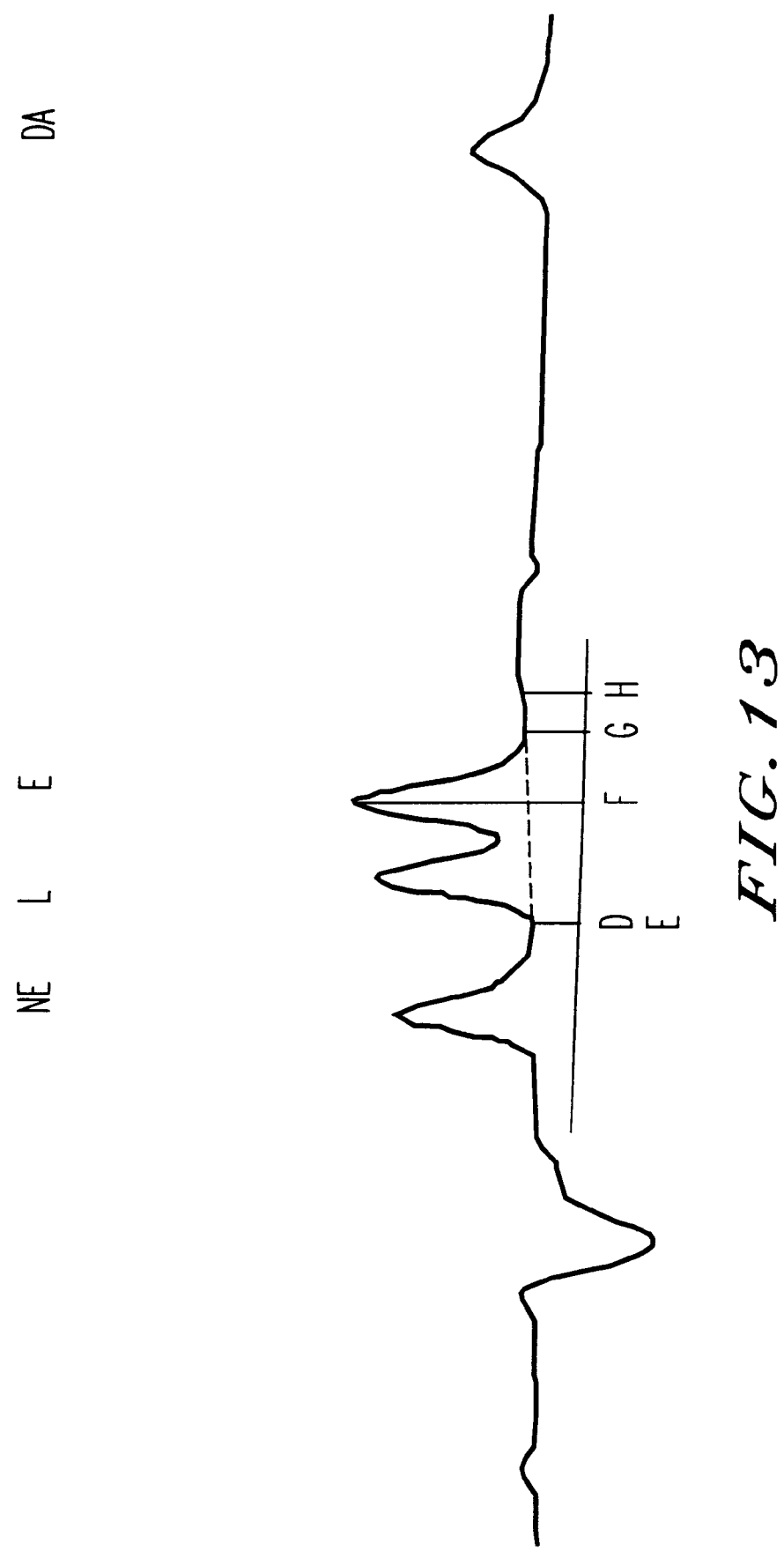
FIG. 13 shows the baseline determined by the analyzer of the present invention in an analysis of the peak attributable to a catecholamine, epinephrine.
Figure 14:
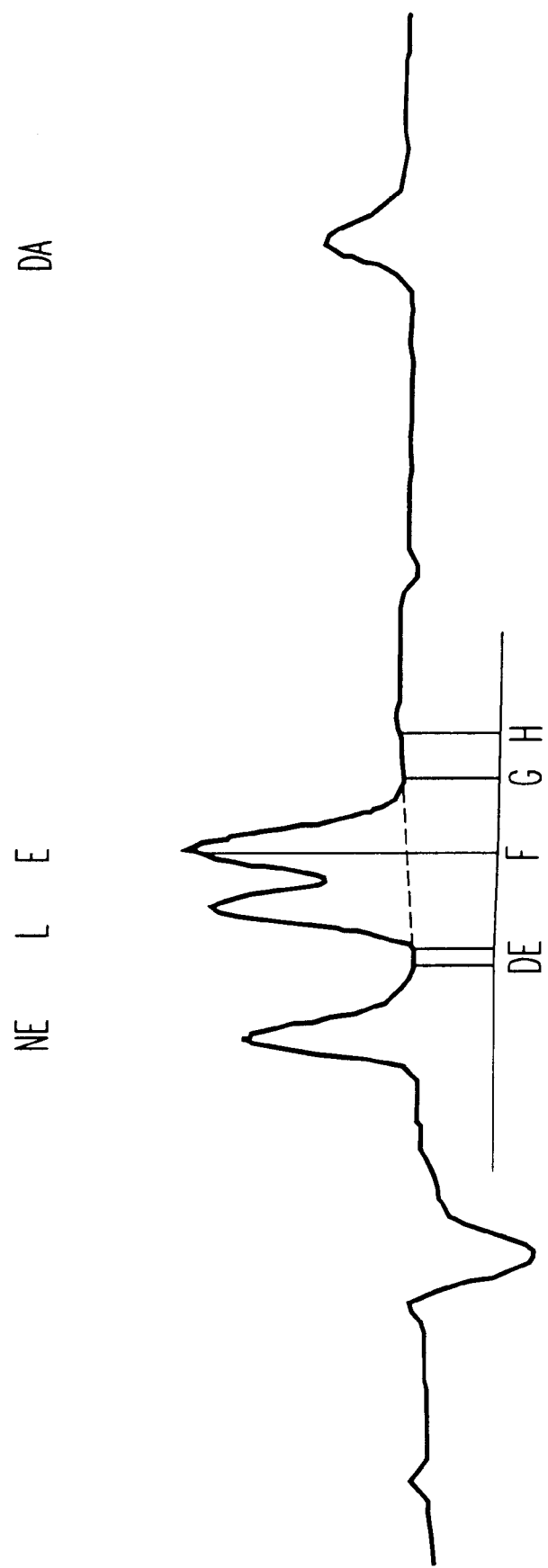
FIG. 14 shows the baseline determined by the analyzer of the present invention in an analysis of the peak attributable to a catecholamine, epinephrine.

The chromatograms were analyzed by a conventional analyzer by detecting the E peak within 0.5 min of ts (ts=19.95 min for FIG. 8, ts=18.66 min for FIG. 9, ts=18.17 min for FIG. 10 and ts=17.79 min for FIG. 11) obtained from chromatograms of a standard sample and joining the points twice the half width before and behind the peak emergence time, tx (B) (0.9 min before and after tx) as the first baseline point (A) and the second baseline point (C), respectively, to give a straight line as the baseline (the dashed line). FIG. 8, FIG. 9, FIG. and FIG. 11 show the results of the same liquid chromatographic operation at 14.5° C., at 22.5° C., at 25.2° C. and at 27.4° C., respectively.

As is evident from the figures, a baseline appropriate for the E peak analysis was given at 14.5° C. (FIG. 8) and at 27.4° C. (FIG. 11), whereas only an inappropriate baseline was given at 22.5° C. (FIG. 9) and at 25.2° C. (FIG. 10).

FIG. 12 to FIG. 15 show the results of analyses of liquid chromatograms for assay of a catecholamine, epimephrine (E) by the analyzer (according to the first aspect) of the present invention. The same sample as described above was used, and the liquid chromatograph used was the same as described above except for the part enclosed with a dashed line in FIG. 1. In the analyses of the chromatograms, the E peaks were detected on the basis of the results obtained from chromatograms of a standard sample (ts=19.95 min, tp1=19.45 min and tp2=20.45 min in FIG. 12, ts=18.66 min, tp1=18.16 min and tp2=19.16 min in FIG. 13, ts=18.17 min, tp1=17.67 min and tp2=18.67 min in FIG. 14, and ts=17.79 min, tp1=17.29 min and tp2=18.29 min in FIG. 15). Then, tb1 (D) were set three times the peak width before the peak emergence times, tx (F) (1.44 minutes before tx), and tb2 (H) were set three times the peak width after the peak emergence times, tx (F). The lowest points (E) of the chromatograms between tb1 and tx were defined as the first baseline points, and the lowest points (G) of the chromatograms between tx and tb2 were defined as the second baseline points, to give the straight lines joining E and G as the baselines (dashed lines). FIG. 12, FIG. 13, FIG. 14 and FIG. 15 show the results of the same liquid chromatographic operation at 14.5° C., at 22.5° C., at 25.2° C. and at 27.4° C., respectively, As is evident from the figures, the analyzer of the present invention gave baselines appropriate for the E peak analysis in all the cases.

EXAMPLE 2

Chromatograms obtained from catecholamines, norepinephrine (NE), epinephrine (E) and dopamine (DA), by liquid chromatography were analyzed by the analyzer of the present invention and a conventional analyzer.

A sample containing NE and DA at 1 pg/ml each was applied to the same liquid chromatograph as used in Example 1 after mixed with an equivalent amount of levonordefrin or dihydroxybenzylamine (DHBA) as a contaminant to give a chromatogram.

In the analysis of the chromatogram by a conventional analyzer, analyte peaks were detected within 0.93 min of ts=16.05 min for NE, within 1.5 min of ts=18.23 min for E and within 3.29 mine of ts=25.11 min for DA on the basis of the result obtained from a chromatogram of a sample containing NE, E and DA only, and then the first baseline points (A) and the second baseline points (C) were provided one, one and a half, two, three or four times the half width (0.41 min for NE, 0.45 min for E and 0.53 min for DA) before and after the peak emergence time tx for each analyte to give the baselines as the straight lines joining A and S. Then, the peak heights for NE, E and DA peaks were determined on the basis of the baselines.

Separately, the same chromatogram was analyzed by the analyzer of the present invention. In the analysis, analyte peaks were detected within 0.465 min of ts=16.05 min (a range of 0.93 min) for NE, within 0.75 min of ts=18.23 min (a range of 1.5 min) for E and within 1.645 min of ts–25.11 min (a range of 3.29 min) for DA on the basis of the result obtained from a chromatogram of a sample containing NE, E and DA only, and then tb1 and tb2 were provided three times the half width (half width: 0.41 min for NE, 0.45 min for E and 0.53 min for DA) before and after the peak emergence time tx for each analyte. Namely, for NE, tb1 was set three times the peak half width before the peak emergence time tx (1.23 min before tx) and tb2 was set three times the peak half width after the peak emergence time tx (1.23 min after tx), for E, tb1 was set three times the peak half width before the peak emergence time tx (1.35 min before tx) and tb2 was set three times the peak half width after the peak emergence time tx (1.35 min after tx), and for DA, tb1 was set three times the peak half width before the peak emergence time tx (1.59 min before tx) and tb2 was set three times the peak half width after the peak emergence time tx (1.59 min after tx), to detect baseline points for determination of baselines. Then, on the basis of the determined baselines, the heights of the NE, E and DA peaks were determined. The results are shown in Table 1.

column 12 is a reversed-phase (ether gel) column of $\phi$ 4.6 mm×75 mm, and the second pre-column 13 is an ion exchange column of $\phi$ 3.0 mm×60 mm) and a separation column 14 which is a reversed-phase (ODS) column ($\phi$4.0 mm×150 mm). In the chromatograph, a sample was carried to the first pre-column by an eluent (phosphate buffer (pH 7)) fed by means of the pump 9a (1.0 ml/min), and then another eluent (a mixture of aqueous ammonium nitride and acetonitrile) was fed to the first pre-column by the pump 9a by switching a solenoid valve to elute the retained sample components onto the second pre-column. Then, the sample components retained on the second pre-column was eluted with an eluent (Tris buffer (pH 7) containing ammonium nitrate) ted by the pump 9b (0.7 ml/min) onto the separation column and separated. The components eluted from the separation column were introduced to the reactor 15 after mixed with a fluorescent reagent and converted into a

TABLE 1

| | | Analyzer of the present invention | | | Conventional analyzer | | | | |
|---|---|---|---|---|---|---|---|---|---|
| | | | | | | 1.5 times | Twice | Three times | Four times |
| | | First aspect | Fourth aspect | Fifth aspect | Peak width | the width | the width | the width | the width |
| NE peak height | Standard solution | 91.33 | 91.71 | 90.43 | 83.31 | 89.63 | 90.6 | 90.92 | 90.52 |
| | SS* + L | 47.16 | 47.97 | 46.45 | 43.05 | 46.7 | 47.15 | 37.41 | 32.34 |
| | SS* + DHBA | 46.12 | 46.57 | 45.49 | 41.86 | 45.33 | 45.82 | 45.8 | 45.31 |
| E peak height | Standard solution | 108.71 | 109.07 | 108.18 | 97.897 | 106.64 | 107.88 | 108.34 | 106.98 |
| | SS* + L | 56.41 | 57.23 | 55.72 | 44.62 | 34.26 | 43.07 | 56.41 | 52.45 |
| | SS* + DHBA | 53.29 | 53.77 | 52.76 | 48.09 | 52.62 | 53.02 | 52.59 | 42.63 |
| DA peak height | Standard solution | 42.72 | 43.12 | 42.27 | 36.46 | 41.32 | 42.54 | 42.38 | 42.06 |
| | SS* + L | 21.46 | 21.53 | 21.35 | 18.56 | 21.01 | 21.21 | 21.18 | 20.84 |
| | SS* + DHBA | 20.69 | 20.93 | 20.45 | 18.21 | 20.39 | 20.68 | 20.38 | 20.14 |
| Ratio of NB peak height | SS* + L | 0.52 | 0.52 | 0.51 | 0.52 | 0.52 | 0.52 | 0.41 | 0.35 |
| | SS* + DHBA | 0.5 | 0.51 | 0.5 | 0.5 | 0.51 | 0.51 | 0.5 | 0.5 |
| Ratio of E peak height | SS* + L | 0.52 | 0.52 | 0.52 | 0.46 | 0.32 | 0.4 | 0.52 | 0.49 |
| | SS* + DHBA | 0.49 | 0.49 | 0.49 | 0.49 | 0.49 | 0.49 | 0.49 | 0.4 |
| Ratio of DA peak height | SS* + L | 0.5 | 0.5 | 0.51 | 0.51 | 0.51 | 0.5 | 0.5 | 0.5 |
| | SS* + DHBA | 0.48 | 0.49 | 0.48 | 0.5 | 0.49 | 0.49 | 0.48 | 0.48 |

SS*: Standard solution

Because the NE, N and DA concentrations in the sample prepared by mixing the standard solution with a contaminant were half the concentrations in the standard solution, and the NE, N and DA peaks in the presence of a contaminant are theoretically half as high as those obtained from the standard solution. As is evident from Table 1, in any aspects of the present invention, the peak height ratios were from 0.48 to 0.52 in good agreement with the theoretical ratio. In contrast, the peak heights obtained by the conventional analyzer diverged from the theoretical value 0.5 even to 0.32. The peak heights of the DA peak obtained by the analyses by the conventional analyzer did not diverged substantially because the DA peak emerged apart from the contaminant peak.

FIG. 3 to FIG. 7 show the results of detection of peaks in a chromatogram obtained by liquid chromatography of catecholamines, norepinephrine (NE), epinephrine (E) and dopamine (DA) by the first arithmetic means. A standard sample containing catecholamines, NE, E and DA at 1 pg/ml each was applied at room temperature (24.6° C.). The NE, E and DA peaks emerged at about 16 min, about 18.5 min and about 25.5 min, respectively. The liquid chromatograph used was equipped with two pre-columns (the first prefluorescent derivative by the reaction with DPE (diphenylethylenediamine) as the fluorescent reagent at 90° C. for 3 minutes in the reactor. The fluorescent reagent was fed by means of the pump 10a and the pump 10b (0.25 ml/min each). The fluorescent derivatives of the analytes were monitored by a fluorometric detector at an excitation wavelength of 340 to 360 nm and an emission wavelength of 460 nm to give a chromatogram.

With respect to FIG. 3 to FIG. 7, the chromatogram was analyzed by using the level of the chromatogram at a particular point as the only variable (FIG. 3 and FIG. 6) or by using the level, the slope, the curvature of the chromatogram and tx as the variables (FIG. 4, FIG. 5 and FIG. 7) for determination of baseline points. The negative peak before the NE peak and the negative peak between the E and DA peaks (indicated by arrows) are ghost peaks which emerged due to switching valve operations in the chromatograph.

In the figures, P is the NE peak detected by the first arithmetic means, tb1 and tb2 are the baseline detection starting time and the baseline detection ending time stored in the first storage means for determination of the baseline for the NE peak, and B is the detected baseline point.

Figure 3:
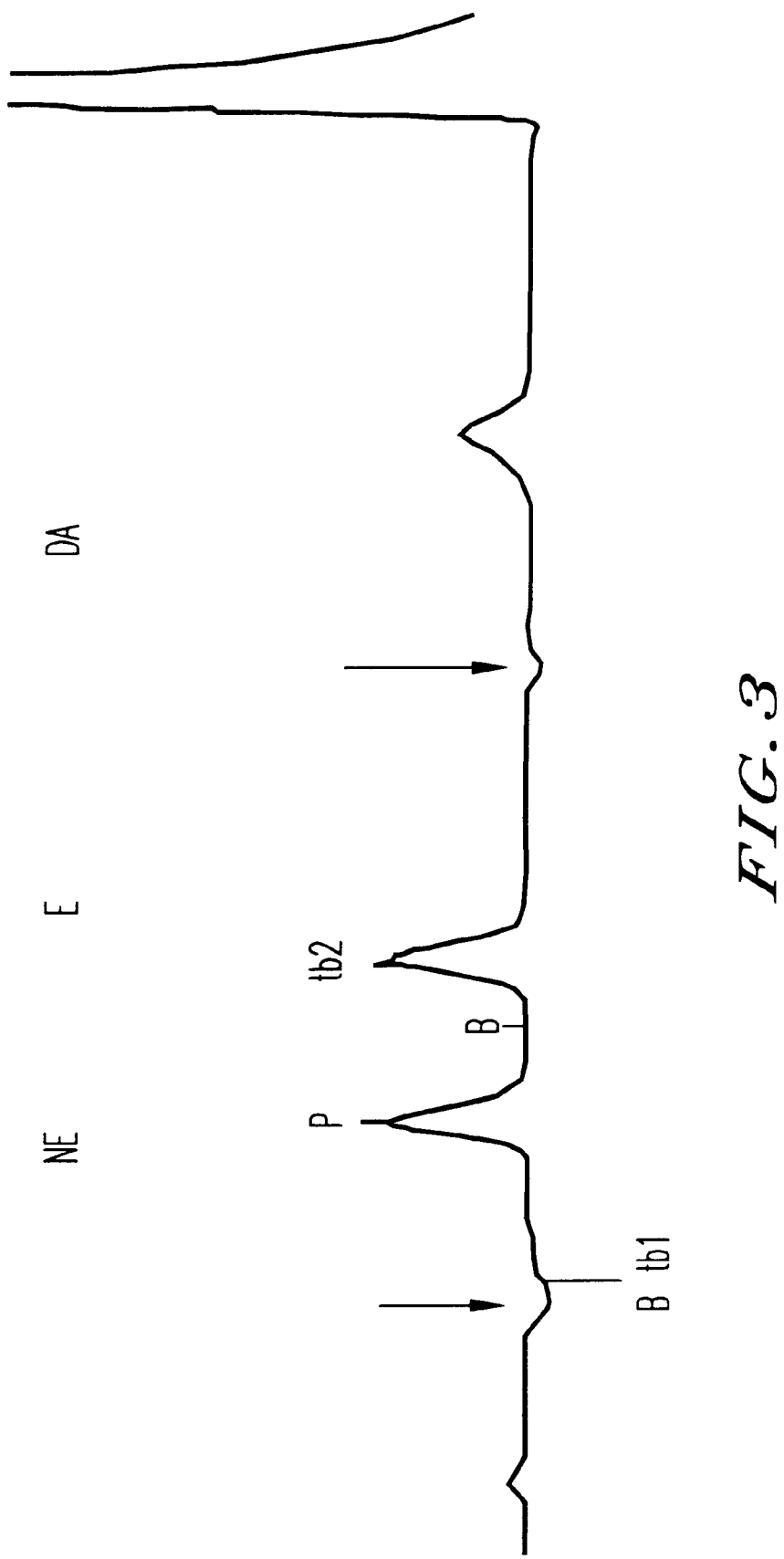
FIG. 3 is a graphic explanation of detection of the baseline points for the peak attributable to a catecholamine, norepinephrine (NE).

FIG. 3 shows the result of baseline detection in which tb1 and tb2 were set 5 times the peak half width before and after tx. In this case, the lowest points of the chromatogram between tb1 and tx and between tx and tb2 were detected as the first and second baseline points.

In this case, proper baseline points were detected for E and DA, though the baseline points are omitted in FIG. 3. For NE, the second baseline point was detected at a proper position despite the presence of the E peak behind the NE peak, but the first baseline point was affected by a negative peak and set on a slope of the ghost peak. Therefore, the peak area and height of the NE peak were calculated inaccurately, though slightly.

Figure 4:
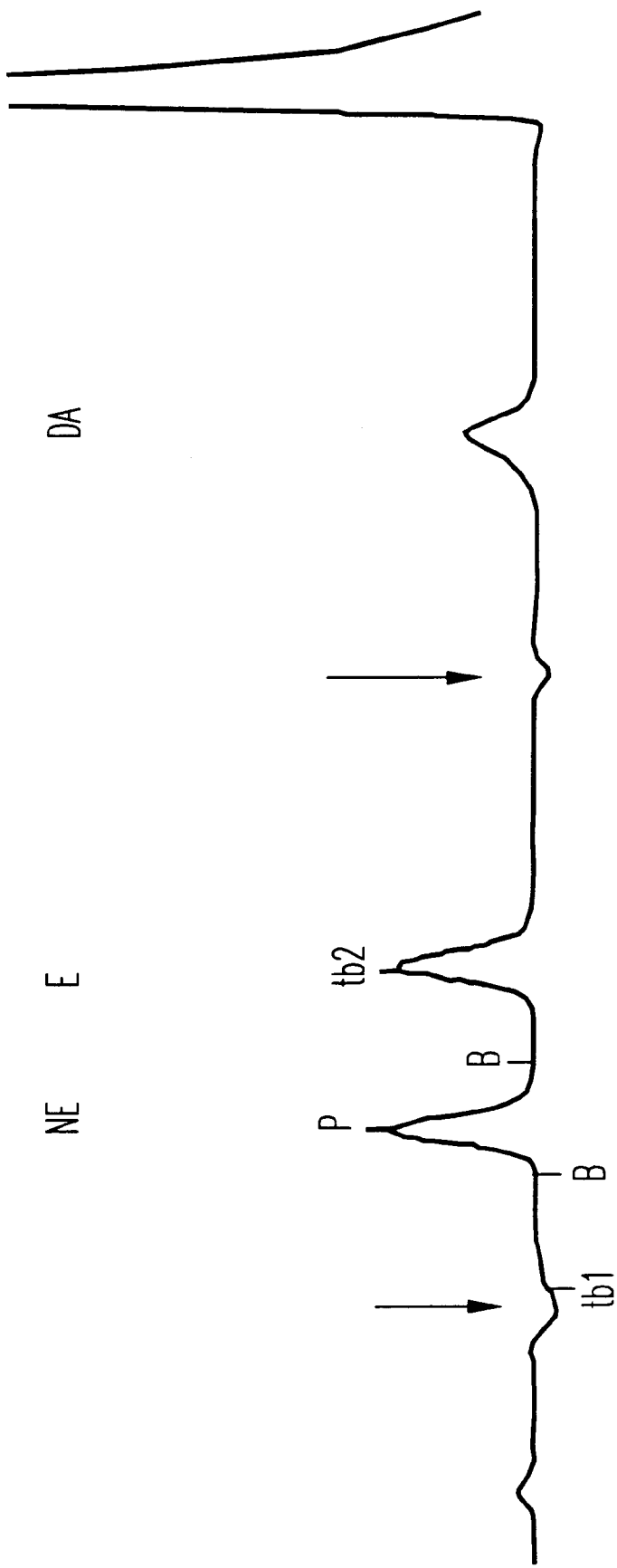
FIG. 4 is a graphic explanation of detection of the baseline points for the peak attributable to a catecholamine, norepinephrine by the analyzer of the present invention.

FIG. 4 illustrates detection of baseline points by the analyzer according to the first aspect of the present invention. The second storage means stored the same chromatogram as shown in FIG. 3. In this case, tb1 and tb2 were set 5 times the peak half width before and after tx and stored in the first storage means. The second arithmetic means detected the points between tb1 and tx and between tx and tb2 which minimized the function=the level of the chromatogram at a particular point+c×(((t−tx)/(tb1−tx))$^4$) as the first and second baseline points.

The parameter c in the function was determined so as to be of the same order as the minimum detectable peak height.

In this case, the baseline points were detected near the NE peak, unlike in the case shown in FIG. 3 in which the first baseline point was detected on the slope of a negative ghost peak due to the influence of the ghost peak.

Figure 5:
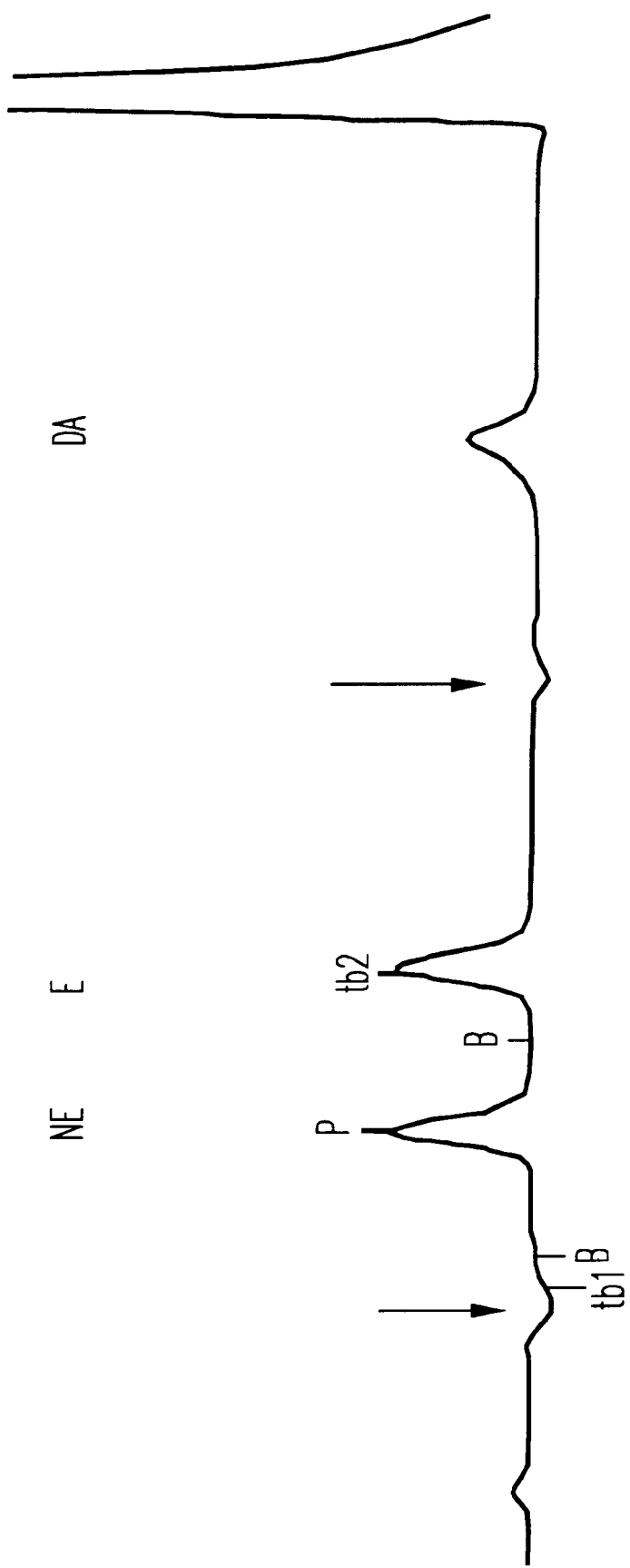
FIG. 5 is a graphic explanation of detection of the baseline points for the peak attributable to a catecholamine, norepinephrine by the analyzer of the present invention.

FIG. 5 illustrates another example of detection of baseline points by the analyzer according to the first aspect of the present invention. The second storage means stored the same chromatogram as shown in FIG. 3.

In this case, tb1 and tb2 were set 5 times the peak half width before and after tx and stored in the first storage means. The second arithmetic means detected the points between tb1 and tx and between tx and tb2 which minimized the function=the level of the chromatogram at a particular point+a×(the absolute slope of the chromatogram) as the first and second baseline points.

The parameter a in the function was determined so that the value of a×(the absolute slope of the chromatogram) would be almost the same as the reference of the level at which the tangent to the chromatogram at the point with the maximum slope is expanded over 30 seconds.

In this case, the baseline points were detected near the NE peak, unlike in the case shown in FIG. 3 in which the first baseline point was detected on the slope of a negative ghost peak due to the influence of the ghost peak.

Figure 6:
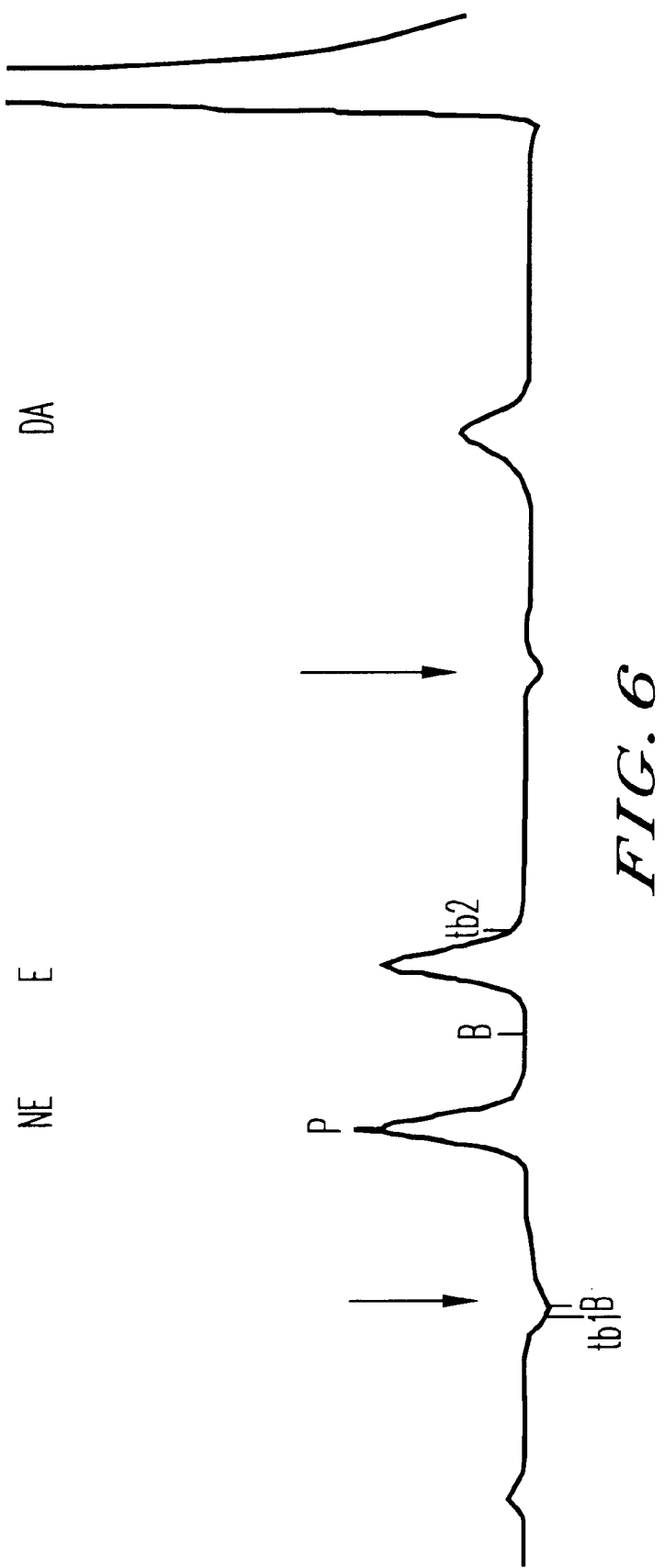
FIG. 6 is a graphic explanation of detection of the baseline points for the peak attributable to a catecholamine, norepinephrine.

FIG. 6 illustrates detection of baseline points in the chromatogram shown in FIG. 3 in which tb1 and tb2 were set 6 times the peak half width from tx. In this case, the lowest points between tb1 and tx and between tx and tb2 were detected as the first and second baseline points.

In this case, the first baseline point was affected by a negative peak and set on a slope of the ghost peak. Therefore, the peak area and height of the NE peak were calculated inaccurately, though slightly.

Figure 7:
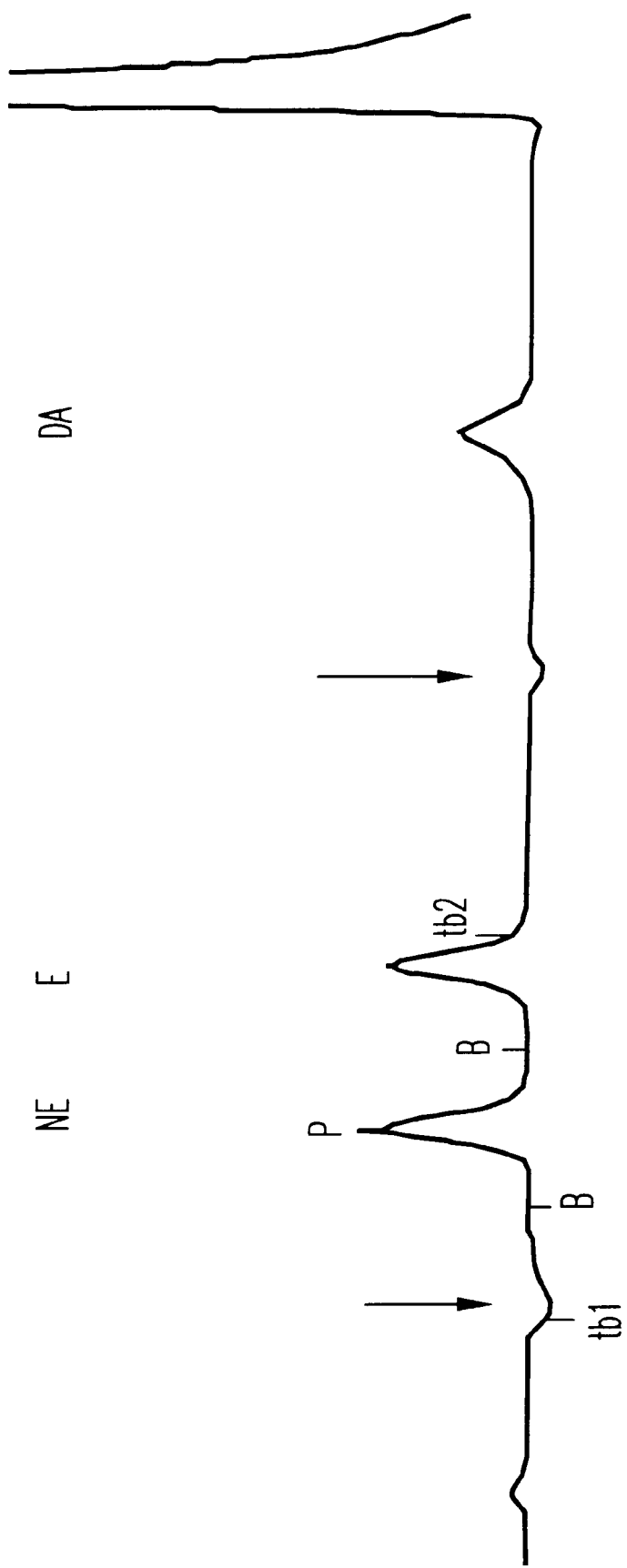
FIG. 7 is a graphic explanation of detection of the baseline points for the peak attributable to a catecholamine, norepinephrine by the analyzer of the present invention.

FIG. 7 illustrates detection of baseline points by the analyzer according to the first aspect of the present invention. The second storage means stored the same chromatogram as shown in FIG. 3. tb1 and tb2 were set 6 times the peak half width before and after tx and stored in the first storage means. The second arithmetic means detected the points between tb1 and tx and between tx and tb2 which minimized the function=the level of the chromatogram at a particular point+a×(the absolute slope of the chromatogram)+b×(the absolute curvature of the chromatogram)+c×(((t−tx)/(tb1−tx))$^4$) as the first and second baseline points.

The parameter a in the function was determined so that the value of a×(the absolute slope of the chromatogram) would be almost the same as the reference of the level at which the tangent to the chromatogram at the point with the maximum slope is expanded over 30 seconds, the parameter b was determined so that the value of b×(the absolute curvature of the chromatogram) would be almost the same as the reference of level at which the quadratic curve approximating the vicinity of the dip of the ghost peak changes at the point 10 seconds away from the dip, and the parameter c was determined so as to have the magnitude of the same order as the minimum detectable peak height (wherein c was set at half the parameter c for FIG. 4).

In this case, despite the presence of a negative ghost peak between tb1 and tx, the first baseline point was not detected at the dip of the ghost peak due to the ghost peak, unlike in the case shown in FIG. 6.

According to the present invention, it is possible to determine more proper baselines in analyses of chromatograms obtained by liquid chromatography, gas chromatography and electrophoresis even if contaminant peaks or ghost peaks emerge before or behind an analyte peak. Therefore, it is possible to determine the heights and areas of analyte peaks more accurately by removing the influence of contaminant peaks or ghost peaks.

Especially, when a negative peak emerges at a various position near an analyte peak depending on temperature or other conditions, the present invention makes it possible to automatically remove the influence of a negative ghost peak, though baselines have been determined from the operator's experience so as to remove the influence.

What is claimed is:

1. A chromatogram analyzer which analyzes a chromatogram obtained by applying a sample containing an analyte, which comprises:

a first storage means which stores a baseline detection starting time (tb1) and a baseline detection ending time (tb2) (wherein tb1<tb2) for determination of a baseline used for analysis of an analyte peak, a second storage means which stores a chromatogram of the analyte, a first arithmetic means which detects an analyte peak and its emergence time (tx, wherein tb1<tx<tb2) on the chromatogram, and a second arithmetic means which detects a first baseline point between tb1 and tx by using a function having at least one of the level, the slope, the curvature and the gap from tx of the chromatogram at a particular point as the variables, detects a second baseline point between tx and tb2 by using a function having at least one of the level, the slope, the curvature and the gap from tx of the chromatogram at a particular point as the variables and gives a straight line passing through the first baseline point and the second baseline point as the baseline.

2. A chromatogram analyzer which analyzes a chromatogram obtained by applying a sample containing an analyte, which comprises:

a first storage means which stores a baseline detection starting time (tb1) and a baseline detection ending time (tb2) (wherein tb1<tb2) for determination of a baseline used for analysis of an analyte peak, a second storage means which stores a chromatogram of the analyte, a first arithmetic means which detects an analyte peak and its emergence time (tx, wherein tb1<tx<tb2) on the chromatogram, and a second arithmetic means which detects a first baseline point between tb1 and tx by using a function having at least one of the level, the slope, the curvature and the gap from tx of the chromatogram at a particular point as the variables, defines the point on the chromatogram at tb2 as a second baseline point and gives a straight line passing through the first baseline point and the second baseline point as the baseline.

3. A chromatogram analyzer which analyzes a chromatogram obtained by applying a sample containing an analyte, which comprises:

a first storage means which stores a baseline detection starting time (tb1) and a baseline detection ending time (tb2) (wherein tb1<tb2) for determination of a baseline used for analysis of an analyte peak, a second storage means which stores a chromatogram of the analyte, p1 a first arithmetic means which detects an analyte peak and its emergence time (tx, wherein tb1<tx<tb2) on the chromatogram, and a second arithmetic means which defines the point on the chromatogram at tb1 as a first baseline point, detects a second baseline point between tx and tb2 by using a function having at least one of the level, the slope, the curvature and the gap from tx of the chromatogram at a particular point as the variables and gives a straight line passing through the first baseline point and the second baseline point as the baseline.

4. A chromatogram analyzer which analyzes a chromatogram obtained by applying a sample containing an analyte, which comprises:

a first storage means which stores a baseline detection starting time (tb1) for determination of a baseline used for analysis of an analyte peak, a second storage means which stores a chromatogram of the analyte, a first arithmetic means which detects an analyte peak and its emergence time (tx, wherein tb1<tx) on the chromatogram, and a second arithmetic means which detects a baseline point between tb1 and tx by using a function having at least one of the level, the slope, the curvature and the gap from tx of the chromatogram at a particular point as the variables and gives a straight line parallel to the time axis and passing through the baseline point as the baseline.

5. A chromatogram analyzer which analyzes a chromatogram obtained by applying a sample containing an analyte, which comprises:

a first storage means which stores a baseline detection ending time (tb2) for determination of a baseline used for analysis of an analyte peak, a second storage means which stores a chromatogram of the analyte, a first arithmetic means which detects an analyte peak and its emergence time (tx, wherein tx<tb2) on the chromatogram, and a second arithmetic means which detects a baseline point between tx and tb2 by using a function having at is least one of the level, the slope, the curvature and the gap from tx of the chromatogram at a particular point as the variables and gives a straight line parallel to the time axis and passing through the baseline point as the baseline.

6. The analyzer according to any one of claims 1 to 3, wherein the first arithmetic means stores beforehand a reference peak emergence time (ts) at which an analyte peak is predicted to emerge on the chromatogram, and when there is a difference between the peak emergence time (tx) of an analyte peak and the reference peak emergence time (ts), adds the difference (tx–ts) to the previously stored tb1 and tb2 before determination of the baseline point.

7. The analyzer according to claim 4 or 5, wherein the first arithmetic means stores beforehand a reference peak emergence time (ts) at which an analyte peak is predicted to emerge on the chromatogram, and when there is a difference between the peak emergence time (tx) of an analyte peak and the reference peak emergence time (ts), adds the difference (tx–ts) to the previously stored tb1 or tb2 before determination of the baseline points.

8. The analyzer according to any one of claims 1 to 5, wherein the function(s) has the level of the chromatogram at a particular point as a variable and increases with increase of the variable and decreases with decreases of the variable, or decreases with increase of the variable and increases with decreases of the variable, and the second arithmetic means determines a point on the chromatogram which minimizes or maximizes the function as a baseline point.

9. The analyzer according to any one of claims 1 to 5, wherein the function(s) has at least one of the level, the slope, the curvature and the gap from tx of the chromatogram at a particular point as the variables and increases with increase of the variable and decreases with decreases of the variable, or decreases with increase of the variable and increases with decreases of the variable, and the second arithmetic means determines a point on the chromatogram which minimizes or maximizes the function as a baseline point.

10. The analyzer according to any one of claims 1 to 5, wherein the function(s) has at least three of the level, the slope, the curvature and the gap from tx of the chromatogram at a particular point as the variables and increases with increase of the variable and decreases with decreases of the variable, or decreases with increase of the variable and increases with decreases of the variable, and the second arithmetic means determines a point on the chromatogram which minimizes or maximizes the function as a baseline point.

11. The analyzer according to any one of claims 1 to 5, wherein the function(s) has the level, the slope, the curvature and the gap from tx of the chromatogram at a particular point as the variables and increases with increase of the variable and decreases with decreases of the variable, or decreases with increase of the variable and increases with decreases of the variable, and the second arithmetic means determines a point on the chromatogram which minimizes or maximizes the function as a baseline point.

* * * * *